United States Patent [19]

Moore

[11] Plant 4,027

[45] Mar. 29, 1977

[54] ROSE PLANT

[76] Inventor: Ralph S. Moore, 2519 E. Noble Ave., Visalia, Calif. 93277

[21] Appl. No.: 651,952

[22] Filed: Jan. 23, 1976

[51] Int. Cl.[2] ..... A01H 5/00
[52] U.S. Cl. ..... Plt./10
[58] Field of Search ..... Plt./10

*Primary Examiner*—Robert E. Bagwill

EXEMPLARY CLAIM

1. A new and distinct variety of miniature rose plant of hardy, dwarf, rounded, much branched, bush type, as illustrated and described, characterized by buds and flowers of a color similar to Baccara (a greenhouse florist variety, H.T. rose) and in plant habit and flower size being similar to Pink Mandy, (miniature); the bud and flower color also resembling Fire Princess (miniature) but being of considerably darker shade, the general color effect being a dark red with a fluorescent orange undertone; the small buds having sepals which are noticeably longer than average with frilled or serrated edges; and further characterized by a plant which is vigorous and compact, the shoots and branches having very short internodes, said plant being easy to propagate from cuttings, with small glossy foliage, an abundance of bloom, with flowers borne singly or several to the stem in loose clusters.

1 Drawing Figure

1

The present invention relates to a new and distinct variety of hardy, dwarf, bush type rose plant of the miniature class; the variety being primarily characterized — as to novelty — by deep red to orange-red buds and flowers which in general color effect are similar in color to Baccara, H.T. variety (U.S. Plant Pat. No. 1,367, expired); also similar to, but deeper red than, Fire Princess, miniature (U.S. Plant Pat. No. 3,084).

The variety is further characterized by:

An abundance of bloom, with flowers borne singly or several to the stem in loose clusters.

Uniquely frilled sepals.

Little or no fragrance.

A plant which is vigorous, of rounded spreading shape and with glossy, very small foliage with pointed leaflets; the buds and flowers being similar in form to Fire Princess and in size to the variety Pink Mandy (U.S. Plant patent applied for).

The plant, which has a normal height of 6 to 8 inches can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Visalia, Calif., under conditions of careful control and observation, as a cross between Little Chief, miniature, not patented as the seed parent and Fire Princess (miniature) as the pollen parent.

Subsequent to origination of the variety I successfully asexually reproduced it, in my nursery located as aforesaid, by budding as well as by cuttings; the reproductions having run true in all respects.

The color photograph illustrates the variety, including foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

2

Type: Hardy; dwarf; bush; seedling; greenhouse; outdoors; cut flowers; garden decoration; potted plant.

Class: Miniature.

Flowers:

*Continuity.*—Continuous — repeat bloom all season.

*Fragrance.*—Little or none.

Flowers borne: Singly and several together (3 to 5) on slender, wirey, short stems.

Quantity of bloom: Abundant both outside and in greenhouse.

Bud: Peduncle — medium length; slender but sturdy; erect; medium green, sometimes tinted bronze; hairs — usually none. Before calyx breaks; size — small. Form medium long; pointed with numerous foliaceous appendages and few or no hairs on surface of bud; with foliaceous parts extending beyond the tip of the bud equal to one-half or more of its length. Color — medium green, occasionally tinted with bronze. As calyx breaks, color — deep red. As first petal opens: same general color; size — small.

Bloom:

*Size when fully open.*—Small, averaging about 20–25 mm.

*Petalage.*—Double — 18–25 petals, arranged regularly plus sometimes several small petolids.

*Form.*—Cupped at first, becoming more open in the center, with petals waved and rolled loosely outward, and later at maturity open with petals rolled loosely outward and downward. Open flowers generally show yellow stamens which give pleasing contrast with petal color.

Petals: Fairly thick; velvety on inside and satiny on outside.

*Shape.*—Outside petals, broad lanceolate with rounded tip; intermediate — broad lanceolate with rounded tip; inside — lanceolate with rounded tip.

Color: Newly opened flower from a plant grown in plastic greenhouse (January, 1976), Visalia, Calif.

*Outside petal.*—Outside surface — near Cardinal Red 822 with some darker shading and small near-white area at base; inside surface — near Cardinal Red 822 with some darker shading and with small near white area at base.

*Intermediate Petal.*—Outside surface — near Cardinal Red 822 with some darker shading and small near white area at base; inside surface — near Cardinal Red 822 with some darker shading and small near white area at base.

*Inner Petal.*—Outside surface — same as intermediate petal; inside surface — same as intermediate petal. General color effect newly opened flowers — deep red with orange (Fluorescent) undertone, similar to Baccara. Three days open — color similar to newly opened flower. Behavior — as flowers age petals may become darker shade before dropping off. In warmer weather and high light intensity the red color is lighter and the orange undertone is more pronounced. Spent petals drop off. Flower longevity (October, 1975) — plant in pot 5–8 days or longer. Cut flowers at living room temperature 4 to 6 days.

Reproductive Organs:

*Stamens.*—Abundant, arranged regularly about pistil.

*Filaments.*—Short, white to pale yellow.

*Anthers.*—Well formed; yellow.

*Pollen.*—Little or none.

*Pistils.*—Average number.

*Styles.*—Fairly even; short; bunched; color — near white tinted red.

*Stigma.*—Nearly white or pale pink.

*Ovaries.*—All enclosed in calyx.

*Hips.*—None.

*Sepals.*—Permanent; spear shaped; lightly recurved.

*Seeds.*—None.

Foliage:

*Leaves.*—Compound of five (often seven) leaflets; abundant; quite small; leathery; glossy.

*Leaflets.*—Shape: Broad, nearly oval; apex acute; base rounded or rounded acute. Margin serrate. Color: normal green; new growth — normal (medium) green. Rachis: medium strength; upper side may have several tiny short prickles, grooved; underside sparsely thorny with few or no tiny prickles. Stipules: medium long; medium width with hairy or serrated edges; medium length narrow points which turn out usually at less than 45°.

Growth:

*Habit.*—Dwarf; bushy; rounded; much branched.

*Growth.*—Free vigorous; internodes very short.

*Canes.*—Medium; slender; sturdy.

*Main stems.*—Color — dull green. Thorns — quite thorny; usually small; hooked slightly downwards; color — brown. Prickles: none. Hairs: none.

Branches: Color — medium green. Thorns — moderately thorny, short length; slender; nearly straight. Medium to short oval base. Prickles — none. Hairs — none.

New shoots: Color — medium green; thorns: moderate; medium length; nearly straight, reddish color; sharp points; base oval. Prickles — none. Hairs — none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, rounded, much branched, bush type, as illustrated and described, characterized by buds and flowers of a color similar to Baccara (a greenhouse florist variety, H.T. rose) and in plant habit and flower size being similar to Pink Mandy, (miniature); the bud and flower color also resembling Fire Princess (miniature) but being of considerably darker shade, the general color effect being a dark red with a fluorescent orange undertone; the small buds having sepals which are noticably longer than average with frilled or serrated edges; and further characterized by a plant which is vigorous and compact, the shoots and branches having very short internodes, said plant being easy to propagate from cuttings, with small glossy foliage, an abundance of bloom, with flowers borne singly or several to the stem in loose clusters.

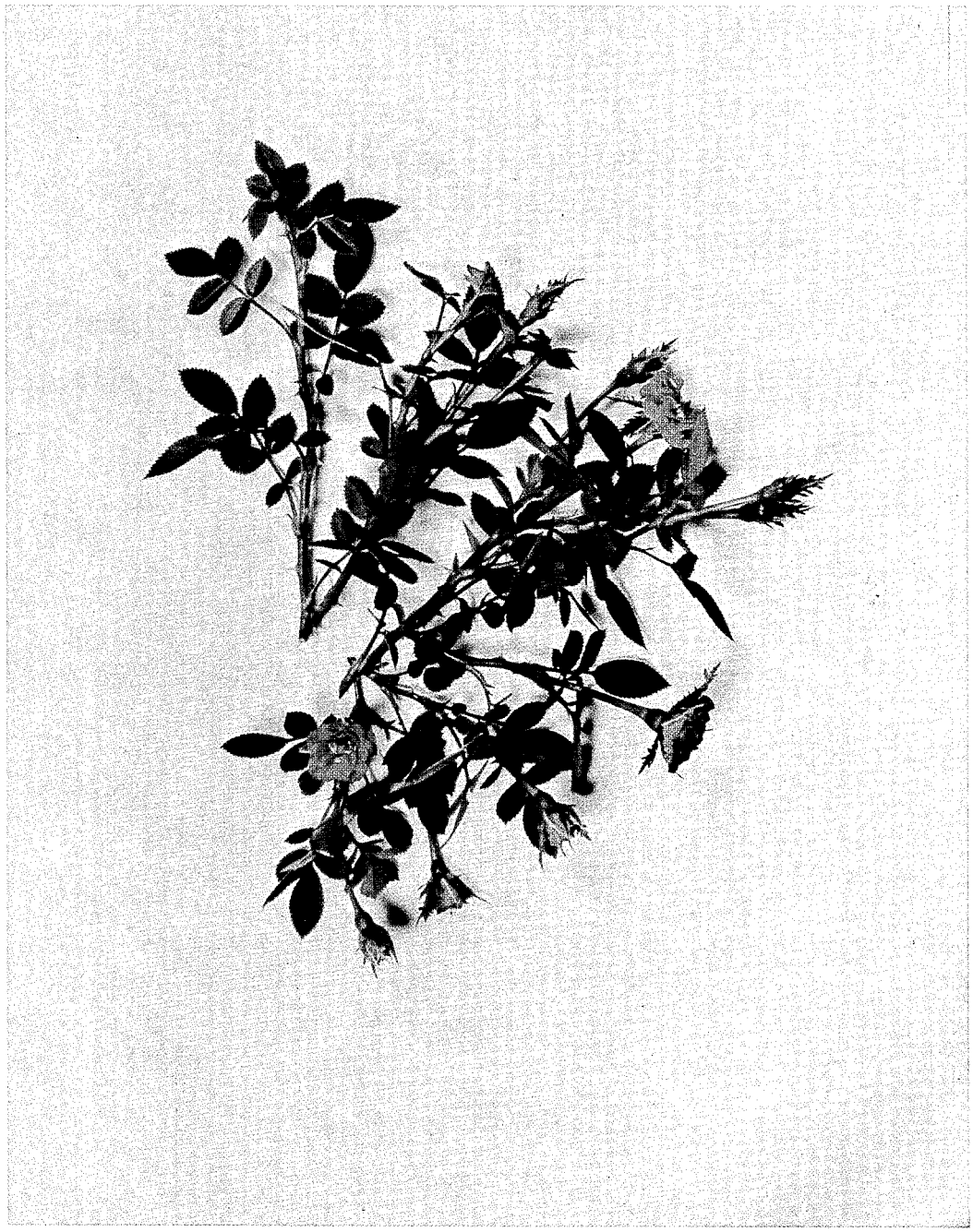

* * * * *